Figure 1:
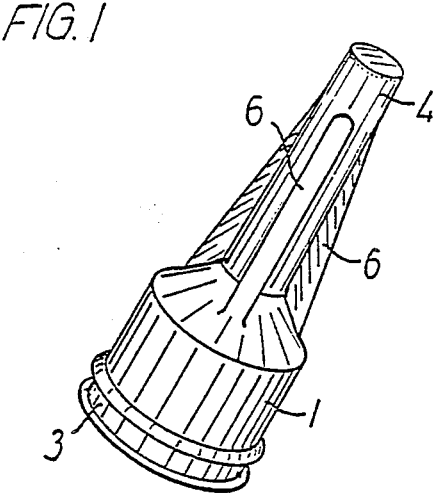

United States Patent [19]

Larsen et al.

[11] Patent Number: 4,894,059
[45] Date of Patent: Jan. 16, 1990

[54] CATHETER APPLICATOR FOR URINARY INCONTINENCE EQUIPMENT

[75] Inventors: J. K. Larsen, Allerod; Michael Morris, Copenhagen, both of Denmark

[73] Assignee: Coloplast A/S, Denmark

[21] Appl. No.: 60,392

[22] PCT Filed: Sep. 22, 1986

[86] PCT No.: PCT/DK86/00105
§ 371 Date: May 22, 1987
§ 102(e) Date: May 22, 1987

[87] PCT Pub. No.: WO87/01582
PCT Pub. Date: Mar. 26, 1987

[30] Foreign Application Priority Data

Sep. 24, 1985 [DK] Denmark .............................. 4317/85

[51] Int. Cl.$^4$ ............................................. A61F 5/44
[52] U.S. Cl. ..................................... 604/349; 206/229
[58] Field of Search ............... 128/132 R, 138 R, 760, 128/761, 767, 842, 844; 206/69, 229; 604/349, 350, 351, 352, 353, 317, 346, 347

[56] References Cited

U.S. PATENT DOCUMENTS

| | | | |
|---|---|---|---|
| 1,301,708 | 4/1917 | Knutson | 604/346 |
| 2,567,926 | 9/1951 | Dunkelberger | 128/844 |
| 2,670,736 | 3/1954 | Dunkelberger | 128/132 R |
| 2,904,041 | 9/1959 | Brown | 128/844 |
| 3,403,682 | 10/1968 | McDonell | 604/352 |
| 3,421,507 | 1/1969 | Gresham | 604/349 |
| 4,140,108 | 2/1979 | Nugent | 128/760 |
| 4,230,115 | 10/1980 | Walz, Jr. et al. | 604/349 |
| 4,500,314 | 2/1985 | Brendling | 604/349 |
| 4,540,409 | 9/1985 | Nystrom et al. | 604/349 |
| 4,589,874 | 5/1986 | Ricdel et al. | 604/349 |

FOREIGN PATENT DOCUMENTS

| | | | |
|---|---|---|---|
| 2120102 | 11/1983 | United Kingdom | 604/349 |
| 2125294 | 3/1984 | United Kingdom | 604/349 |

Primary Examiner—C. Fred Rosenbaum
Assistant Examiner—Mario Costantino
Attorney, Agent, or Firm—Ostrolenk, Faber, Gerb & Soffen

[57] ABSTRACT

A male urinary incontinence device includes an external male catheter joined to an applicator therefor. The male catheter includes a draining portion and a rolled-up body portion which may be unrolled to form a substantially cylindrical body portion of elastic material. The applicator may include a substantially cylindrical tubular member comprising a material having greater rigidity than the catheter. The tubular member may have an opening for receiving at least the drainage portion of the catheter and preferably part of the body portion. The applicator may be include a means such as a groove along the circumference of its external surface for retaining a rolled-up portion of the catheter. A closed-end gripping member, capable of accommodating the drainage portion of the catheter is preferred, as is a covering member along the opening of the applicator.

7 Claims, 1 Drawing Sheet

CATHETER APPLICATOR FOR URINARY INCONTINENCE EQUIPMENT

The invention relates to an applicator for the arrangement of an external catheter of a male urinary incontinence equipment, said catheter being of the kind comprising a soft elastic thin-walled, substantially cylindrical body portion which is open at one end and is joined at the other end with a narrowed drainage tube portion for connection with a collection bag, said catheter being supplied to the user with the body portion rolled up from the open end towards the drainage tube end, said applicator comprising an annular or tubular member of a resilient thin-walled material having a greater rigidity than the catheter and being designed for arrangement externally on the catheter.

For catheters of this kind having the shape of condoms problems frequently occur in practice with respect to the arrangement of the catheter as a result of the fact that the catheter which is delivered in a rolled-up condition and, having regard to the comfort of the user, is manufactured from a thin-walled very flexible latex material, is to be arranged on a normal flaccid penis. Since the users of such articles are often elderly persons under nursery or disabled persons, the arrangement must frequently be performed by the nursing personnel, but this in addition to hygienic problems is often considered psychically embarrassing to the users.

In order to remedy these disadvantages an applicator for use in the arrangement of an external catheter has been suggested in international patent application, publication No. WO81/03609. The applicator is delivered to the user with the catheter arranged on it in a flat condition so that a rather great application of pressure is required in use for expanding the opening of the applicator which might be difficult for elderly or disabled users.

Moreover, from SE published patent application No. 362,584 an applicator is known formed as a cylindrical envelope having two parts which are axially displaceable relative to each other, and in which the expansion of the catheter for its arrangement is conditional upon the generation of a subpressure by drawing out the inner part of the applicator. This known applicator which accommodates the catheter in its entire extension has a length which makes it less suitable for disposable use, and also in this case the operation requires a certain exercise of force.

On this background it is the object of the invention to provide an aiding means for use in the arrangement of the catheter with which a substantially simplified and safer arrangement of the catheter is obtained so that the arrangement may more frequently be performed by the user himself, even by patients suffering from reduced finger movability.

According to the invention this is achieved by means of an applicator which is characterized in that the annular or tubular member is designed so as to surround the catheter through an axial length from the transition between the body portion and the drainage tube portion corresponding substantially to the length of the penis glans, the end of said member facing the open end of the body portion being designed to retain the rolled-up portion of the catheter in the supply condition, whereas the drainage tube portion of the catheter is accommodated in a closed narrowed tube portion formed in extension of said annular or tubular member. By means of this applicator which is delivered as a disposable article together with the catheter the arrangement is performed in a simple way in that the drainage tube end of the catheter surrounded by said annular or tubular element is placed on the penis glans and held against it by a slight external pressure on the element itself without any contact with the off from the rolled-up supply condition, since the resilient thin-walled applicator has such an increased rigidity relative to the catheter that it stabilizes the shape of the drainage tube end of the catheter upon arrangement around the penis glans and, moreover, covers the glans due to its axial extension so that the rolling-off will take place over the length of penis on which thickness variations do substantially not occur.

Additionally, it has turned out that the applicator according to the invention which can be used both in connection with catheters at the arrangement of which a separate adhesive strip is first wound around the penis and in the case of so-called "one-piece" products having an integral adhesive coating on the inner side of the catheter results in an improved product uniformity in the production of the catheter in which the rolling-up to the supply condition is performed on a mandrel. The applicator may simply be arranged on the drainage tube end on the catheter arranged on the mandrel, thereby ensuring a uniform rolling-up, where the rolled-up part is retained at the said end of the applicator facing the open end of the body portion. As a result thereof the rolling-up may easily be performed on a cylindrical mandrel.

As a result of the design of the applicator with a closed narrowed tube part formed in extension of said annular or tubular element for accommodating the drainage tube portion of the catheter the applicator furthermore makes up an emballage protecting the rolled-up catheter in the supply condition and thus preventing contamination of the catheter and the risk of infection following therefrom. The narrowed tube part may be substantially cylindrical and formed with a number of external longitudinal ribs which are used as a finger grip during arrangement.

Figure 4:
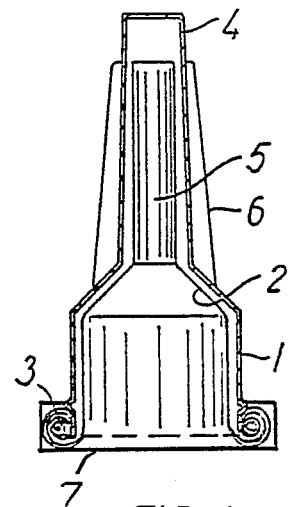
Figure 2:
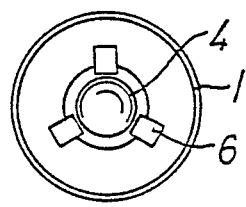
Figure 3:
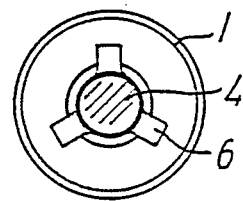

In the following the invention will be further explained with reference to an embodiment shown on the accompanying drawing, in which FIG. 1 is a perspective view of an applicator, FIGS. 2 and 3 show the applicator as viewed from the closed and open ends, respectively, and FIG. 4 is a sectional view of the applicator arranged on an external catheter.

As shown, the applicator comprises an annular or tubular element 1 which is designed for arrangement around a catheter 2 in the rolled-up supply condition thereof.

The element is manufactured with such dimensions and such a shape that in the arrangement of the rolled-up catheter on a penis it will substantially surround the catheter through an axial length corresponding to the length of the penis glans.

As shown in FIG. 1 the element 1 may be formed with a circumferential groove 3 for retaining the rolled-up part of the catheter 2. Thereby, a good localization of the rolled-up part is obtained when rolling up the catheter, as the applicator is arranged outside the catheter while it is positioned on the mandrel on which the rolling-up is performed.

In the embodiment shown the applicator comprises in extension of the element 1 a closed narrowed tube portion 4 for accommodating the drainage tube portion 5 of the catheter 2. Thereby the applicator provides a closed emballage for the rolled-up catheter which is thereby protected against mechanical injury as well as contamination and the risk of infection following therefrom. The opening of the applicator and the rolled-up part of the catheter 2 located around it may in this connection be covered by a covering member, 7 not shown, e.g. of metal foil.

The tube portion 4 serves, moreover, to further facilitate the arrangement of the catheter on the penis since it is formed with a number, in this case three, external longitudinal ribs 6 which may serve as a finger grip.

The applicator with the annular tubular element 1 and the tube portion 4 is manufactured from a thin-walled material having a greater rigidity than the catheter, e.g. as a vacuum shaped member of PVC. Thereby, the applicator will simultaneously stabilize the form of the drainage tube portion of the catheter and through its resiliency provide a possibility of safely holding the catheter against a flaccid penis before arrangement by a slight external pressure on the applicator whereby contact with the very thin-walled catheter is avoided. Simultaneously, the form of the applicator with a length of the element 1 so as to surround the glans throughout its length will facilitate the rolling-off which is then to take place only over the part of penis on which there are substantially no thickness variations.

Instead of the circumferential groove 3 providing a limitation at both sides, the open end of the applicator may possibly only have a bead for localizing the rolled-up part of the catheter 2 in which case there may, however, be a certain risk of positioning the rolled-up part of the catheter during the rolling-up at a greater distance than desired from the open end of the applicator and thus of a less uniform product.

We claim:

1. A male urinary incontinence device comprising a male catheter for external application which includes a draining portion and a rolled-up portion, said rolled-up portion being capable, of unrolling into a substantially cylindrical body of elastic material open at an end farthest from said drainage portion for receiving a male penis; and in contact with said catheter, an applicator having a substantially cylindrical tubular member comprised of material having greater rigidity than said catheter, said tubular member having an opening for receiving part of said catheter other than said rolled-up portion and said tubular member further having an external surface which includes a means for contacting and retaining said rolled-up portion of said male catheter in a position along an outer circumference of said tubular member and of retarding the unrolling of said rolled-up portion until said rolled-up portion is unrolled by a user, said tubular member including a hollow gripping member having an internal cavity capable of encircling the entire length of said drainage portion of said catheter.

2. The male urinary incontinence device of claim 1 wherein said means for retaining said rolled-up portion of said catheter is a groove.

3. The male urinary incontinence device of claim 2 wherein said gripping member is substantially cylindrical and has a number of external longitudinal ribs.

4. The male urinary incontinence device of claim 2 further comprising a covering member along the opening of said applicator to restrict access to the interior thereof.

5. The male urinary incontinence device of claim 1 wherein said gripping member is substantially cylindrical and has a number of external longitudinal ribs.

6. The male urinary incontinence device of claim 5 further comprising a covering member along the opening of said applicator to restrict access to the interior thereof.

7. The male urinary incontinence device of claim 1 further comprising a covering member along the opening of said applicator to restrict access to the interior thereof.

* * * * *